United States Patent
Kenny et al.

(10) Patent No.: US 12,029,557 B1
(45) Date of Patent: Jul. 9, 2024

(54) RADIO FREQUENCY ANTENNA FOR WEARABLE DEVICE

(71) Applicant: AMAZON TECHNOLOGIES, INC., Seattle, WA (US)

(72) Inventors: Justin Christopher Kenny, Redmond, WA (US); Adrian Napoles, Bellevue, WA (US); Andreas Caduff, Clyde Hill, WA (US); Christopher Raymond Grajewski, Sammamish, WA (US); David Heckerman, Bellevue, WA (US)

(73) Assignee: AMAZON TECHNOLOGIES, INC., Seattle, WA (US)

( * ) Notice: Subject to any disclaimer, the term of this patent is extended or adjusted under 35 U.S.C. 154(b) by 627 days.

(21) Appl. No.: 17/116,368

(22) Filed: Dec. 9, 2020

(51) Int. Cl.
| | |
|---|---|
| *A61B 5/145* | (2006.01) |
| *A61B 5/00* | (2006.01) |
| *A61B 5/053* | (2021.01) |
| *H01Q 1/27* | (2006.01) |
| *H04B 1/3827* | (2015.01) |
| *H04B 17/10* | (2015.01) |

(52) U.S. Cl.
CPC .......... *A61B 5/14546* (2013.01); *A61B 5/053* (2013.01); *A61B 5/6824* (2013.01); *H01Q 1/273* (2013.01); *H04B 1/385* (2013.01); *H04B 17/104* (2015.01); *A61B 5/14532* (2013.01); *A61B 5/4845* (2013.01); *A61B 5/4875* (2013.01)

(58) Field of Classification Search
CPC . A61B 5/14532; A61B 5/6824; A61B 5/4845; A61B 5/4875; H01Q 1/273
See application file for complete search history.

(56) References Cited

U.S. PATENT DOCUMENTS

| | | | |
|---|---|---|---|
| 11,398,671 B2 * | 7/2022 | Bien | A61B 5/145 |
| 2010/0112614 A1 * | 5/2010 | Axelrod | C12Q 1/54 |
| | | | 435/14 |
| 2013/0303868 A1 * | 11/2013 | Fischer | A61B 5/14532 |
| | | | 600/365 |
| 2019/0008422 A1 * | 1/2019 | Leath | A61B 5/14532 |
| 2019/0104939 A1 * | 4/2019 | Costantine | A61B 5/14532 |

* cited by examiner

*Primary Examiner* — Eric F Winakur
(74) *Attorney, Agent, or Firm* — Lindauer Law, PLLC

(57) ABSTRACT

Data about concentration of one or more types of molecules present within a human body are determined noninvasively using radio frequency signals. Signals at several different frequencies at very low power levels are emitted using an antenna mounted to a wearable device. The antenna includes nested elements of different sizes. Operating values, such as changes to the impedance of the antenna, are associated with the concentration of one or more types molecules within the user. Concentrations at different depths may be measured by using different sets of the nested elements at different times. Operating values at those times are measured and used to determine information indicative of concentration of the molecules. During use, a long axis of the antenna may be aligned with a long axis of a user's arm.

20 Claims, 9 Drawing Sheets

RADIO FREQUENCY ANTENNA FOR WEARABLE DEVICE

BACKGROUND

Physiological data may be used to help a user manage their health, make more informed decisions, and improve the quality of their life. For example, physiological data such as hydration level, glucose concentration, and so forth may be useful for health management.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features.

Figure 1:
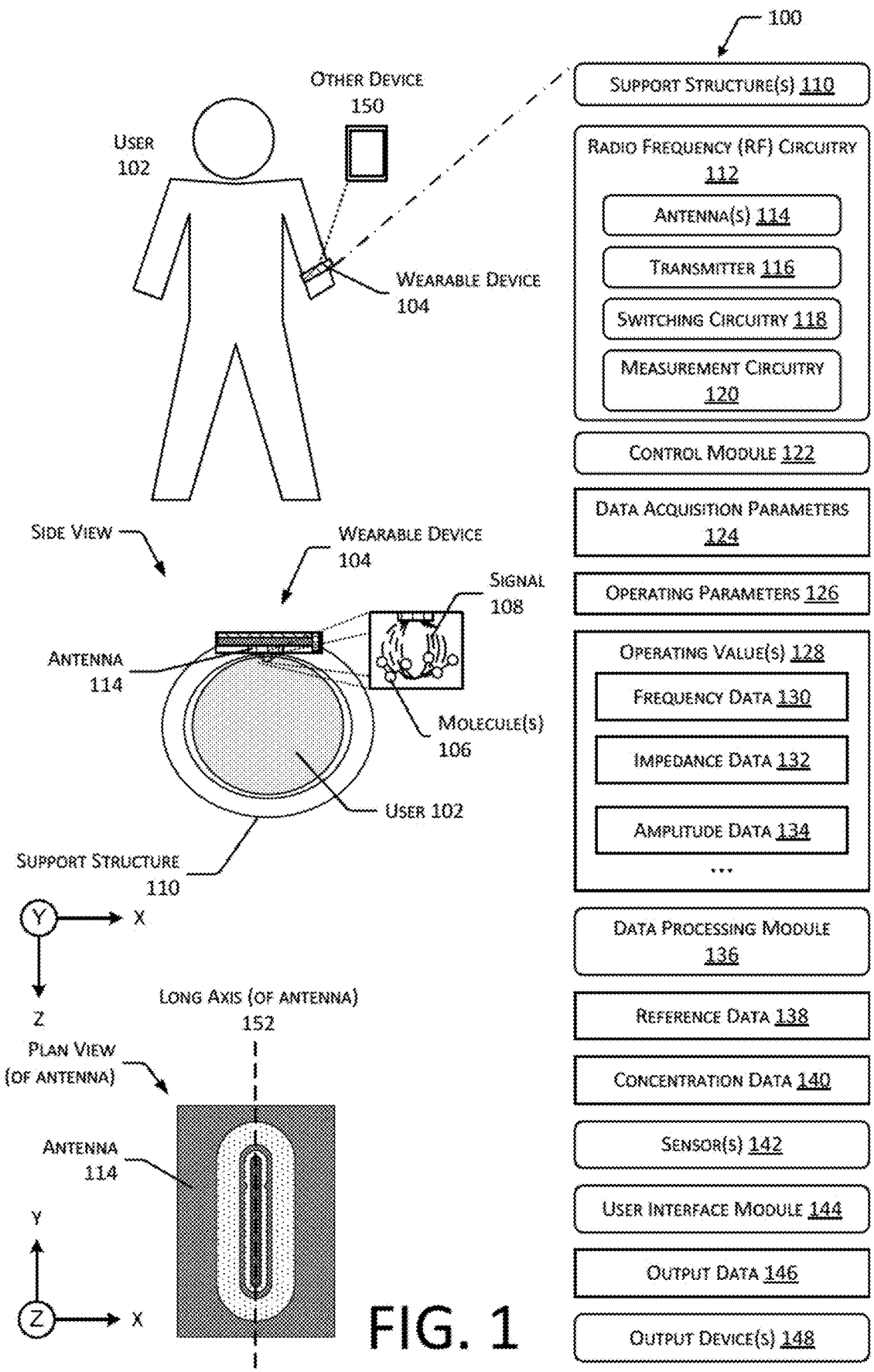
FIG. 1 is an illustrative system that includes a wearable device with an antenna that uses radio frequency signals to determine molecular concentrations of molecules of interest in the user, according to one implementation.

While implementations are described herein by way of example, those skilled in the art will recognize that the implementations are not limited to the examples or figures described. It should be understood that the figures and detailed description thereto are not intended to limit implementations to the particular form disclosed but, on the contrary, the intention is to cover all modifications, equivalents, and alternatives falling within the spirit and scope as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including, but not limited to.

The structures depicted in the following figures are not necessarily according to scale. Furthermore, the proportionality of one component to another may change with different implementations. In some illustrations the scale or a proportionate size of one structure may be exaggerated with respect to another to facilitate illustration, and not necessarily as a limitation.

DETAILED DESCRIPTION

The human body utilizes many different kinds of molecules to function. For example, glucose provides energy for cellular activity while water provides a medium to carry molecules such as glucose and also acts as a reactant. Other molecules may be introduced into the body. For example, alcohol may be consumed, carbon monoxide may be inhaled, a pesticide may be absorbed through the skin, and so forth.

Information about the concentration of one or more types of molecules within the tissues of the body is useful in many situations. For example, a person who is diabetic needs to know the concentration of glucose in their blood in order to keep that concentration in a healthy range. In another example, an athlete needs to make sure they are sufficiently hydrated to maximize their physical performance and avoid injury due to dehydration. Continuing the example, the athlete may also want to monitor their sodium and potassium levels to maintain an optimal level of electrolytes.

Traditionally information about the concentration of one or more types of molecules has been obtained through invasive measurement of a sample obtained from the person. For example, to measure glucose levels a sample of blood is taken and applied to a chemical test strip. In another example, a rough estimate of dehydration can be obtained by assessing skin turgor, such as by pinching the skin on the back of the hand. However, traditional methods have significant drawbacks. Obtaining samples of blood or other tissues within the body requires piercing the skin, injuring the person and introducing a possibility of infection. Additionally, such testing can be costly due to special handling considerations, use of consumables such as reagents, and so forth. Mechanical measurements, such as assessment of skin turgor, lack precision.

Described in this disclosure is an antenna that facilitates non-invasively measuring molecular concentration of one or more types of molecules within a user. A very low power radio frequency (RF) signal is emitted from an antenna, with the electromagnetic field from the antenna impinging upon a portion of the user. The presence of different concentrations of molecules will interact with this electromagnetic field and introduce changes in operating values, such as impedance of the antenna. In one implementation, measurement circuitry may determine changes in impedance of the antenna due to changes in the nearby portion of the user that are within the electromagnetic field from the antenna.

The antenna comprises several nested antenna elements. For example, the antenna may comprise a first antenna element surrounded by a second antenna element, a third antenna element may surround the second antenna element, and so forth. The overall shape of the antenna may be an elongated oval or "racetrack" pattern, with a long axis extending through a long axis of the elongated oval. In some implementations, during use the long axis of the antenna may be arranged to parallel a long axis of an arm or leg of the user. This arrangement may improve the quality of data obtained by minimizing variations in output of the operating values due to motion of the user.

By selectively using particular antenna elements, different electromagnetic field shapes may be produced. These different field shapes extend different distances from the antenna, allowing information to be obtained about different depths within the user. For example, use of a first antenna element may produce a first field that extends a first distance "D1" from the antenna, while use of the first and second antenna elements may produce a second field that extends a second distance "D2" from the antenna where D2 is greater than D1. Continuing the example, use of the first, second, and third antenna elements may produce a third field that extends a third distance "D3" from the antenna, where D3 is greater than D2. In one implementation, D3 may be approximately 2 millimeters.

The antenna is able to operate in conjunction with other sensors. Apertures, or other sensor elements, may be arranged between the antenna elements. For example, the antenna elements may be on a substrate. One or more apertures in the substrate between the antenna elements may provide a window for other sensors to operate. For example, an optical heart rate monitor may operate by sensing the user's skin using light sent through the aperture. In another example other sensors such as an optical emitter and an optical receiver may be located on the substrate between the antenna elements.

The system includes radio frequency (RF) circuitry that may include the antenna, a transmitter, switching circuitry, measurement circuitry, and so forth. During operation of the system, the switching circuitry selectively connects output from the RF transmitter to a particular set of antenna elements in the antenna. The RF transmitter generates a first signal at a first frequency that is emitted from the set of antenna elements of the antenna. Measurement circuitry determines one or more operating values associated with the operation of the RF transmitter. The operating values may include information such as frequency data indicative of the frequency of the generated signal, impedance data indicative of impedance presented by the antenna, amplitude data, and so forth. For example, the measurement circuitry may determine an impedance presented by the antenna to the first signal. At different times, different sets of antenna elements may be used to acquire information about different depths within the user.

The RF circuitry may utilize different frequencies at different times. For example, the RF transmitter may generate signals in different frequency bands, providing operating values for the different bands. For example, the first signal may be transmitted at 50 megahertz (MHz), a second signal at 5 gigahertz (GHz), a third signal at 5 kilohertz (KHz), a fourth signal at 100 GHz, and so forth.

The operating values may be compared to reference data to determine one or more of presence of or concentration of one or more types of molecules present within the user. In one implementation, the impedance presented at different frequencies may be used to determine a concentration of a type of molecule, such as glucose. For example, the molecular concentration data may describe a linear relationship between impedances at particular frequencies and glucose concentration. In other implementations, the concentration of other types of molecules may be determined. For example, the concentration of water may be determined, providing information about a hydration level of the user.

Overall exposure to radio frequency (RF) signals is limited, as the output power is extremely low and duration of the radio frequency (RF) signals may be very short. For example, the modulation of the signals may be a continuous wave with a total duration of less than 1 millisecond (ms) and with a transmitter output power of 0 decibel-milliwatts (dBm). The sampling frequency, that is how often the RF signals are transmitted to gather data, may also be low, further reducing RF exposure. For example, the system may transmit signals once every six minutes, producing sets of ten samples per hour with each set comprising operating value data for the various frequency bands.

By using the system with the antenna and techniques described in this disclosure, information about the concentration of various types of molecules at different depths within the user may be determined non-invasively. The ability to dynamically adjust the sample depth improves the ability for the system to obtain data. For example, due to anatomical differences, information about glucose levels may be obtained from a first user at a first sample depth and from a second user at a second sample depth. The system may use the antenna to acquire data from the sample depth that provides useful data. In another example, different molecules may be preferentially located at different depths. For example, hydration may be determined based on the presence of water in the upper layers of the skin at a relatively shallow sample depth while sodium concentration in the blood may be determined based on a relatively deep sample depth that includes larger arteries and veins.

The information provided by the system may be used to help diagnose, treat, or inform the user as to their physiological status. By acting on this information, the overall health of the user may be improved.

Illustrative System

FIG. 1 is an illustrative system 100 that may include a user 102 and a wearable device 104 that uses radio frequency (RF) signals to determine molecular concentrations of molecules of interest in at least a portion of the user's body, according to one implementation.

The user 102 may have one or more devices on or about their person, such as the wearable device 104. The wearable device 104 may be implemented in various physical form factors including, but not limited to, the following: wrist bands, torcs, arm bands, ankle bands, abdominal straps, and so forth.

The user's 102 body contains one or more different types of molecules 106. For example, the blood of the user 102 may include glucose, water, creatinine, and so forth. Sometimes the body may include molecules 106 that are exogenous. For example, if the user 102 consumes alcohol, inhales carbon monoxide, absorbs a pesticide through the skin, and so forth, presence or concentration of those types of molecules 106 may be present in the dermis, within the blood, or other tissues within the body. As described below, a radio frequency (RF) signal 108 may be used to determine information about one or more molecules 106.

The wearable device 104 may include at least one support structure 110 that supports one or more of the following components. For example, the wearable device 104 may comprise a housing or capsule that is attached to a wrist band, allowing the wearable device 104 to be retained on the wrist of the user 102 as shown in FIG. 1. In another example, the wearable device 104, or a portion thereof, may comprise an adhesive patch to adhere to the user 102 during operation. Also shown in FIG. 1 is a side view of the wearable device 104 as shown worn on the arm. An enlarged view shows the signal 108 and the molecules 106.

The wearable device 104 includes radio frequency (RF) circuitry 112 that includes one or more antennas 114, a transmitter 116, switching circuitry 118, measurement circuitry 120, and may include other circuitry. The antennas 114 may comprise one or more antenna elements in particular arrangements. For example, the antenna elements may comprise a first antenna element and one or more antenna elements that are arranged around the first antenna element. As shown in the plan view, the overall arrangement of the antenna 114 may appear as an elongated oval, with a long axis 152 extending through a long axis of the elongated oval. In some implementations, during use the long axis 152 of the antenna may be arranged to parallel a long axis of an arm or leg of the user 102. This arrangement between the antenna 114 and the user 102 may improve the quality of data obtained by minimizing variations in output of the operating values due to motion of the user 102. The arrangement of antenna elements is discussed in more detail below with regard to FIGS. 4 and 5.

The switching circuitry 118 selectively couples the output from the transmitter 116 to one or more of the antenna elements in the antenna 114. The switching circuitry 118 is discussed in more detail with regard to FIG. 7.

The transmitter 116 is configured to generate an RF signal 108. The transmitter 116 may be able to generate RF signals 108 at one or more frequencies, in one or more frequency bands or ranges, and so forth. For example, the transmitter 116 may be able to generate RF signals 108 at one or more of the 1 kHz, 50 MHz, 5 GHz, or other bands. The RF signal 108 that is generated may be modulated with a continuous wave.

During transmission, the transmitter 116 provides the RF signal 108 to the switching circuitry 118 that in turn provides the RF signal 108 to a set of the one or more of the antenna elements of the antenna 114. For example, output from the transmitter 116 may be connected to a first antenna element in the antenna 114 at a first time. The antenna 114 emits the signal 108 which then impinges on the body of the user 102 while the wearable device 104 is being worn or held close to the user 102. At a second time, a second set of the one or more antenna elements of the antenna 114 may be used.

The measurement circuitry 120 determines one or more operating values 128 associated with one or more of the operation of the transmitter 116, the load presented by the antenna 114, and so forth. The operating values 128 may include information such as frequency data 130 indicative of the frequency of the generated signal 108, impedance data 132 indicative of impedance presented by the antenna 114 comprising the set of antenna elements connected via the switching circuitry 118, amplitude data 134 indicative of an amplitude of the RF signal 108, and so forth. For example, the measurement circuitry 120 may determine an impedance presented by the antenna 114 to the first signal at 50 MHz.

While a transmitter 116 is shown, it is understood that in other implementations the RF circuitry 112 may include other components such as receiver, transceiver, and so forth.

A control module 122 may be used to direct operation of the RF circuitry 112 or other components. For example, the control module 122 may comprise a hardware processor (processor) executing instructions that operate the switching circuitry 118 to connect a particular set of antenna elements of the antenna 114 to the transmitter 116, operate the transmitter 116 to transmit particular signals 108 at particular frequencies at particular times, acquire operating values 128 during operation of the transmitter 116, and so forth.

The control module 122 may use one or more data acquisition parameters 124 to control operation. For example, the data acquisition parameters 124 may specify a sample frequency that indicates how often to transmit signals, sample depth within the user 102 to be used, and so forth. In some implementations the data acquisition parameters 124 may be specific to a particular type of molecule 106 that is being detected. For example, the data acquisition parameters 124 for glucose may have a first sample depth that is different from a second sample depth used for organophosphates. The data acquisition parameters 124 may reference specific operating parameters 126.

The operating parameters 126 may specify one or more of frequency, output power, modulation, signal duration, particular antenna elements used to emit the signal 108, particular antenna elements used to acquire the signal 108, and so forth. For example, the operating parameters 126 may specify that a signal is to be transmitted with a center frequency of 50 MHz at 0 dBm, continuous wave (CW) modulation, particular sets of antenna elements to use to obtain data from the desired depths, and so forth.

The operating parameters 126 may relate a sample depth specified by the data acquisition parameters 124 to a particular antenna configuration. For example, the data acquisition parameters 124 may indicate a depth in terms of linear measurement such as millimeters or with a relative indicator such as "shallow", "medium", or "deep". Responsive to the data acquisition parameters 124, the control module 122 may determine operating parameters 126 that are indicative of a particular antenna configuration. For example, a "shallow" sample depth may correspond to an antenna configuration or set of antenna elements in which the first antenna element is connected to the transmitter 116 and used to emit the signal 108. In comparison, a "deep" sample depth may correspond to an antenna configuration or set of antenna elements in which the first antenna element, a second antenna element, and a third antenna element are simultaneously connected to the transmitter 116 and used to emit the signal 108.

Once the operating parameters 126 have been determined, the control module 122 or another component may operate the circuitry in the wearable device 104. For example, the control module 122 may operate at a first time the switching circuitry 118 to selectively connect a first set of antenna elements to the transmitter 116, operate the transmitter 116 to generate a first signal 108 at a first frequency, and operate the measurement circuitry 120 to acquire a first impedance value. Continuing the example, at a second time the switching circuitry 118 may be operated to selectively connect a second set of antenna elements to the transmitter 116, operate the transmitter 116 to generate a second signal 108 at a second frequency, and operate the measurement circuitry 120 to acquire a second impedance value.

As the RF signals 108 as emitted by the antenna 114 impinge on the body of the user 102, they are affected by the molecules 106 therein. Various interactions take place between the signals 108 and the molecules 106. For example, the presence of glucose in the body within the volume encompassed by the electromagnetic field produced by the antenna 114 during operation of the transmitter 116 may result in a change in impedance that the antenna 114 presents to the transmitter 116. As described below, a presence or concentration of a type of molecule 106 may be determined based on the impedance or other operating values.

A data processing module 136 may use one or more of the operating parameters 126 of the transmitted signal(s) 108 or the operating values 128 as input. The data processing module 136 may also access reference data 138. The reference data 138 comprises information that, for a particular type of molecule 106, associates one or more operating values 128 with information such as concentration of the particular type of molecule 106. The reference data 138 may be general or specific to a particular user 102. For example, the reference data 138 may be generated and associated with particular user 102(1) "Pat".

The data processing module 136 may use the operating value(s) 128 and the reference data 138 to determine molecular concentration data 140. The molecular concentration data 140 may specify a mass per unit volume. For example, the operating value 128 indicates the impedance value at a particular frequency is 51.7 ohms at 50 MHz. This value may be used as input to the reference data 138 which corresponds to molecular concentration data 140 indicative of a mass per volume, such as a glucose concentration of 159 milligrams per deciliter (mg/dL).

As described below in more detail, the operating values 128 may be obtained for a plurality of different frequencies and may be obtained using a variety of different sets of antenna elements of the antenna 114 to emit the signals 108. The operating values 128 may be used to determine the molecular concentration data 140 for one or more different types of molecules 106. For example, the molecular concentration data 140 may indicate the concentration of glucose and water in the body of the user 102.

The wearable device 104 may include, or receive data from, one or more other sensors 142. For example, a temperature sensor may be used to provide an indication of the body temperature of the user 102. The body temperature may then be used as an input to the data processing module 136 to improve the accuracy of the molecular concentration data 140. These sensors 142 are discussed in more detail below with regard to FIG. 2. In other implementations data from the sensors 142 may be obtained to provide other information about physiological status, activity level, and so forth.

Output from the sensors 142 may also be used to determine operation of the data processing module 136. For example, the sensors 142 may include one or more accelerometers. If the accelerometers detect motion that exceeds a threshold value, the data processing module 136 may be operated to determine molecular concentration data 140. For example, if the user 102 has been running, the system 100 may operate to determine glucose concentration. In another example, if the motion of the user 102 is less than a threshold value, the data processing module 136 may be operated to determine molecular concentration data 140. For example, if no movement has been detected for 2 minutes, such as if the user 102 is asleep or unconscious, the data processing module 136 may be operated to determine molecular concentration data 140.

A user interface module 144 may be configured to use the molecular concentration data 140 and produce output data 146. For example, based on the molecular concentration data 140 indicating that the blood glucose level is below a threshold value, output data 146 may be generated. One or more output devices 148 may be used to present a user interface based on at least a portion of the output data 146. Continuing the example, the user interface module 144 may produce output data 146 that comprises instructions to operate a speaker to present an audible prompt indicating the low blood glucose level. In another example, the output data 146 may be provided to an other device 150. For example, the wearable device 104 may be connected via Bluetooth or another wireless protocol to a smartphone, wireless access point, in vehicle computer system, or other device. Based on the output data 146 the other device 150 may present an output to the user 102, alert someone else, modify operation of another device, and so forth. For example, if the wearable device 104 provides data to a vehicle that indicates the user 102 in the driver's seat has a concentration of alcohol that exceeds a threshold value, the vehicle may be prevented from moving, or may only be able to operate in a fully autonomous mode.

In other implementations, the wearable device 104, or portions thereof may be incorporated into other devices. For example, at least a portion of the wearable device 104, such as the antenna 114, maybe be incorporated into or attached to a seat, chair, bed, and so forth.

Figure 2:
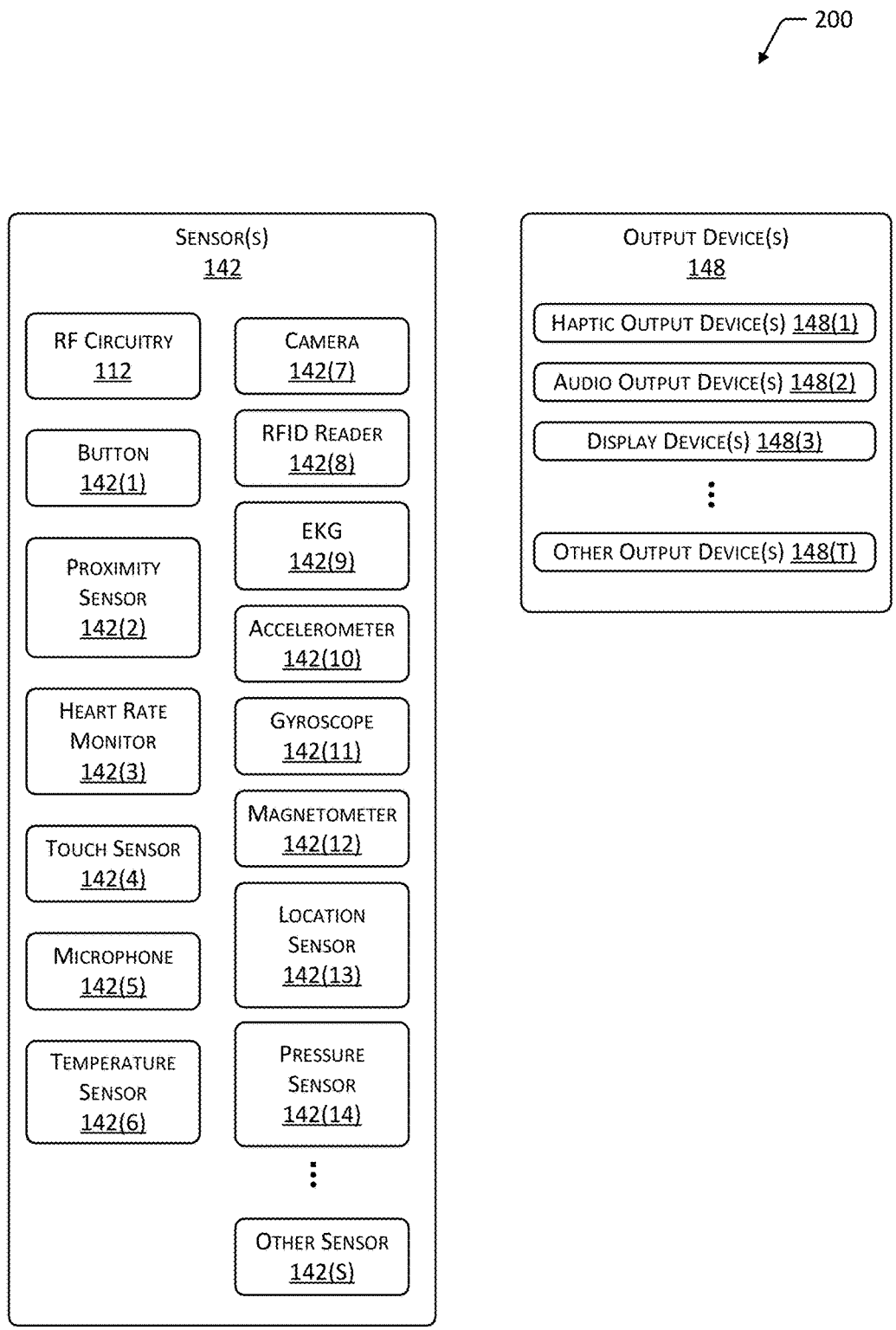
FIG. 2 illustrates a block diagram of sensors and output devices that may be used by computing device(s) during operation, according to one implementation.

FIG. 2 illustrates a block diagram 200 of sensors 142 and output devices 148 that may be used by the devices of the system 100 during operation.

The one or more sensors 142 may be integrated with or internal to the wearable device 104 or the other device 150. For example, the sensors 142 may be built-in to the wearable device 104 during manufacture. In other implementations, the sensors 142 may be part of another device which is in communication with the wearable device 104. For example, the sensors 142 may comprise a device external to, but in communication with, the wearable device 104 using Bluetooth, Wi-Fi, 4G, 5G, LTE, ZigBee, Z-Wave, or another wireless or wired communication technology.

The sensors 142 may include the RF circuitry 112.

The one or more sensors 142 may include one or more buttons 142(1) that are configured to accept input from the user 102. The buttons 142(1) may comprise mechanical, capacitive, optical, or other mechanisms. For example, the buttons 142(1) may comprise mechanical switches configured to accept an applied force from a touch of the user 102 to generate an input signal.

A proximity sensor 142(2) may be configured to provide sensor data 324 indicative of one or more of a presence or absence of an object, a distance to the object, or characteristics of the object. The proximity sensor 142(2) may use optical, electrical, ultrasonic, electromagnetic, or other techniques to determine a presence of an object. For example, the proximity sensor 142(2) may comprise a capacitive proximity sensor configured to provide an electrical field and determine a change in electrical capacitance due to presence or absence of an object within the electrical field.

A heart rate monitor 142(3) or pulse oximeter may be configured to provide sensor data 324 that is indicative of a cardiac pulse rate, data indicative of oxygen saturation of the user's 102 blood, and so forth. For example, the heart rate monitor 142(3) may use an optical emitter such as one or more light emitting diodes (LEDs) and a corresponding optical detector such as a photodetector to perform photoplethysmography, determine cardiac pulse, determine changes in apparent color of the blood of the user 102 resulting from oxygen binding with hemoglobin in the blood, and so forth.

The sensors 142 may include one or more touch sensors 142(4). The touch sensors 142(4) may use resistive, capacitive, surface capacitance, projected capacitance, mutual capacitance, optical, Interpolating Force-Sensitive Resistance (IFSR), or other mechanisms to determine the position of a touch or near-touch of the user 102. For example, the IFSR may comprise a material configured to change electrical resistance responsive to an applied force. The location within the material of that change in electrical resistance may indicate the position of the touch.

One or more microphones 142(5) may be configured to acquire information about sound present in the environment. In some implementations, arrays of microphones 142(5) may be used. These arrays may implement beamforming techniques to provide for directionality of gain. The one or more microphones 142(5) may be used to acquire audio data, such as speech from the user 102.

A temperature sensor (or thermometer) 142(6) may provide information indicative of a temperature of an object. The temperature sensor 142(6) in may be configured to measure ambient air temperature proximate to the user 102, the body temperature of the user 102, and so forth. The temperature sensor 142(6) may comprise a silicon bandgap temperature sensor, thermistor, thermocouple, or other device. In some implementations, the temperature sensor 142(6) may comprise an infrared detector configured to determine temperature using thermal radiation.

The sensors 142 may include one or more cameras 142(7). The cameras 142(7) may comprise a charge couple device, complementary oxide semiconductor, or other image sensor that is able to acquire images.

One or more radio frequency identification (RFID) readers 142(8), near field communication (NFC) systems, and so forth, may also be included as sensors 142. The user 102, objects around the computing device, locations within a building, and so forth, may be equipped with one or more radio frequency (RF) tags. The RF tags are configured to emit an RF signal. In one implementation, the RF tag may be an RFID tag configured to emit the RF signal upon activation by an external signal. For example, the external signal may comprise an RF signal or a magnetic field configured to energize or activate the RFID tag. In another implementation, the RF tag may comprise a transmitter and a power source configured to power the transmitter. For example, the RF tag may comprise a Bluetooth Low Energy (BLE) transmitter and battery. In other implementations, the tag may use other techniques to indicate its presence. For example, an acoustic tag may be configured to generate an ultrasonic signal, which is detected by corresponding acoustic receivers. In yet another implementation, the tag may be configured to emit an optical signal.

The sensors 142 may include an electrocardiograph (EKG) 142(9) that is configured to detect electrical signals produced by the heart of the user 102.

The sensors 142 may include one or more accelerometers 142(10). The accelerometers 142(10) may provide information such as the direction and magnitude of an imposed acceleration. Data such as rate of acceleration, determination of changes in direction, speed, and so forth, may be determined using the accelerometers 142(10).

A gyroscope 142(11) provides information indicative of rotation of an object affixed thereto. For example, the gyroscope 142(11) may indicate whether the device has been rotated.

A magnetometer 142(12) may be used to determine an orientation by measuring ambient magnetic fields, such as the terrestrial magnetic field. For example, output from the magnetometer 142(12) may be used to determine whether the device containing the sensor 142, such as a computing device, has changed orientation or otherwise moved. In other implementations, the magnetometer 142(12) may be configured to detect magnetic fields generated by another device.

A location sensor 142(13) is configured to provide information indicative of a location. The location may be relative or absolute. For example, a relative location may indicate "kitchen", "bedroom", "conference room", and so forth. In comparison, an absolute location is expressed relative to a reference point or datum, such as a street address, geolocation comprising coordinates indicative of latitude and longitude, grid square, and so forth. The location sensor 142(13) may include, but is not limited to, radio navigation-based systems such as terrestrial or satellite-based navigational systems. The satellite-based navigation system may include one or more of a Global Positioning System (GPS) receiver, a Global Navigation Satellite System (GLONASS) receiver, a Galileo receiver, a BeiDou Navigation Satellite System (BDS) receiver, an Indian Regional Navigational Satellite System, and so forth. In some implementations, the location sensor 142(13) may be omitted or operate in conjunction with an external resource such as a cellular network operator providing location information, or Bluetooth beacons.

A pressure sensor 142(14) may provide information about the pressure between a portion of the wearable device 104 and a portion of the user 102. For example, the pressure sensor 142(14) may comprise a capacitive element, strain gauge, spring-biased contact switch, or other device that is used to determine the amount of pressure between the user's 102 arm and an inner surface of the wearable device 104 that is in contact with the arm. In some implementations the pressure sensor 142(14) may provide information indicative of a force measurement, such as 0.5 Newtons, a relative force measurement, or whether the pressure is greater than a threshold value.

In some implementations, operation of one or more components in the wearable device 104 may be based at least in part on information from the pressure sensor 142(14). For example, based on data provided by the pressure sensor 142(14) a determination may be made as to whether at least a portion of the wearable device 104 is in contact with the user 102 or another object. Continuing the example, if the pressure indicated by the pressure sensor 142(14) exceeds a threshold value, the wearable device 104 may be determined to be in contact with the user 102. Based on this determination that the wearable device 104 is in contact with the user 102, one or more of the transmitter 116, receiver, sensors 142, and so forth may be operated. Likewise, data from the pressure sensor 142(14) may be used to determine the wearable device 104 is not in sufficient physical contact with the user 102. As a result, one or more of the transmitter 116, a receiver, sensors 142, and so forth may be turned off.

The sensors 142 may include other sensors 142(S) as well. For example, the other sensors 142(S) may include strain gauges, anti-tamper indicators, and so forth. For example, strain gauges or strain sensors may be embedded within the wearable device 104 and may be configured to provide information indicating that at least a portion of the wearable device 104 has been stretched or displaced such that the wearable device 104 may have been donned or doffed.

In some implementations, the sensors 142 may include hardware processors, memory, and other elements configured to perform various functions. Furthermore, the sensors 142 may be configured to communicate by way of the network or may couple directly with the computing device.

The computing device may include or may couple to one or more output devices 148. The output devices 148 are configured to generate signals which may be perceived by the user 102, detectable by the sensors 142, or a combination thereof.

Haptic output devices 148(1) are configured to provide a signal, which results in a tactile sensation to the user 102. The haptic output devices 148(1) may use one or more mechanisms such as electrical stimulation or mechanical displacement to provide the signal. For example, the haptic output devices 148(1) may be configured to generate a modulated electrical signal, which produces an apparent tactile sensation in one or more fingers of the user 102. In another example, the haptic output devices 148(1) may comprise piezoelectric or rotary motor devices configured to provide a vibration that may be felt by the user 102.

One or more audio output devices 148(2) are configured to provide acoustic output. The acoustic output includes one or more of infrasonic sound, audible sound, or ultrasonic sound. The audio output devices 148(2) may use one or more mechanisms to generate the acoustic output. These mechanisms may include, but are not limited to, the following: voice coils, piezoelectric elements, magnetostrictive elements, electrostatic elements, and so forth. For example, a piezoelectric buzzer or a speaker may be used to provide acoustic output by an audio output device 148(2).

The display devices 148(3) may be configured to provide output that may be seen by the user 102 or detected by a light-sensitive detector such as an image sensor or light sensor. The output may be monochrome or color. The display devices 148(3) may be emissive, reflective, or both. An emissive display device 148(3), such as using light emitting diodes (LEDs), is configured to emit light during operation. In comparison, a reflective display device 148(3), such as using an electrophoretic element, relies on ambient light to present an image. Backlights or front lights may be used to illuminate non-emissive display devices 148(3) to provide visibility of the output in conditions where the ambient light levels are low.

The display mechanisms of display devices 148(3) may include, but are not limited to, micro-electromechanical systems (MEMS), spatial light modulators, electroluminescent displays, quantum dot displays, liquid crystal on silicon (LCOS) displays, cholesteric displays, interferometric displays, liquid crystal displays, electrophoretic displays, LED displays, and so forth. These display mechanisms are configured to emit light, modulate incident light emitted from another source, or both. The display devices 148(3) may operate as panels, projectors, and so forth.

The display devices 148(3) may be configured to present images. For example, the display devices 148(3) may comprise a pixel-addressable display. The image may comprise at least a two-dimensional array of pixels or a vector representation of a two-dimensional image.

In some implementations, the display devices 148(3) may be configured to provide non-image data, such as text or numeric characters, colors, and so forth. For example, a segmented electrophoretic display device, segmented LED, and so forth, may be used to present information such as letters or numbers. The display devices 148(3) may also be configurable to vary the color of the segment, such as using multicolor LED segments.

Other output devices 148(T) may also be present. For example, the other output devices 148(T) may include scent/odor dispensers.

Figure 3:
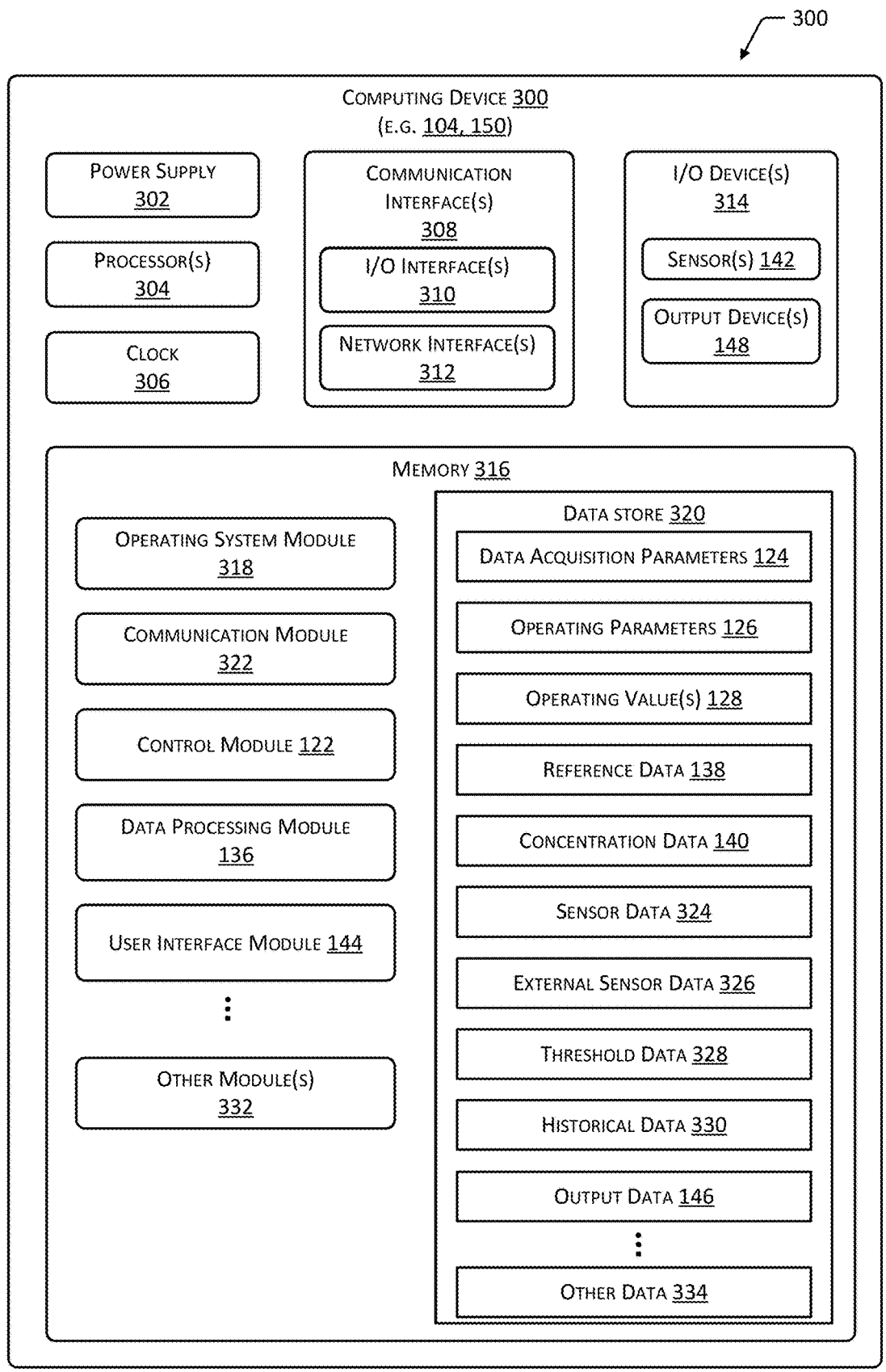
FIG. 3 illustrates a block diagram of a computing device (s) that may be included in or in communication with the wearable device, according to one implementation.

FIG. 3 illustrates a block diagram of a computing device 300 configured to support operation of the system 100. As described above, the computing device 300 may be the wearable device 104, the other device 150, and so forth.

One or more power supplies 302 are configured to provide electrical power suitable for operating the components in the computing device 300. In some implementations, the power supply 302 may comprise a rechargeable battery, fuel cell, photovoltaic cell, power conditioning circuitry, and so forth.

The computing device 300 may include one or more hardware processors 304 (processors) configured to execute one or more stored instructions. The processors 304 may comprise one or more cores. One or more clocks 306 may provide information indicative of date, time, ticks, and so forth. For example, the processor 304 may use data from the clock 306 to generate a timestamp, trigger a preprogrammed action, and so forth.

The computing device 300 may include one or more communication interfaces 308 such as input/output (I/O) interfaces 310, network interfaces 312, and so forth. The communication interfaces 308 enable the computing device 300, or components thereof, to communicate with other devices or components. The communication interfaces 308 may include one or more I/O interfaces 310. The I/O interfaces 310 may comprise interfaces such as Inter-Integrated Circuit (I2C), Serial Peripheral Interface bus (SPI), Universal Serial Bus (USB) as promulgated by the USB Implementers Forum, RS-232, and so forth.

The I/O interface(s) 310 may couple to one or more I/O devices 314. The I/O devices 314 may include input devices such as one or more of a camera 142(7), a sensor 142, keyboard, mouse, scanner, and so forth. The I/O devices 314 may also include output devices 148 such as one or more of a display device 148(3), printer, audio output device 148(2), and so forth. In some embodiments, the I/O devices 314 may be physically incorporated with the computing device 300 or may be externally placed.

The network interfaces 312 are configured to provide communications between the computing device 300 and other devices, such as the sensors 142, routers, access points, and so forth. The network interfaces 312 may include devices configured to couple to wired or wireless personal area networks (PANs), local area networks (LANs), wide area networks (WANs), and so forth. For example, the network interfaces 312 may include devices compatible with Ethernet, Wi-Fi, Bluetooth, ZigBee, 4G, 5G, LTE, and so forth.

The computing device 300 may also include one or more buses or other internal communications hardware or software that allow for the transfer of data between the various modules and components of the computing device 300.

As shown in FIG. 3, the computing device 300 includes one or more memories 316. The memory 316 comprises one or more computer-readable storage media (CRSM). The CRSM may be any one or more of an electronic storage medium, a magnetic storage medium, an optical storage medium, a quantum storage medium, a mechanical computer storage medium, and so forth. The memory 316 provides storage of computer-readable instructions, data structures, program modules, and other data for the operation of the computing device 300. A few example functional modules are shown stored in the memory 316, although the same functionality may alternatively be implemented in hardware, firmware, or as a system on a chip (SOC).

The memory 316 may include at least one operating system (OS) module 318. The OS module 318 is configured to manage hardware resource devices such as the I/O interfaces 310, the network interfaces 312, the I/O devices 314, and provide various services to applications or modules executing on the processors 304. The OS module 318 may implement a variant of the FreeBSD operating system as promulgated by the FreeBSD Project; other UNIX or UNIX-like operating system; a variation of the Linux operating system as promulgated by Linus Torvalds; the Windows operating system from Microsoft Corporation of Redmond, Washington, USA; the Android operating system from Google Corporation of Mountain View, California, USA; the iOS operating system from Apple Corporation of Cupertino, California, USA; or other operating systems.

Also stored in the memory 316 may be a data store 320 and one or more of the following modules. These modules may be executed as foreground applications, background tasks, daemons, and so forth. The data store 320 may use a flat file, database, linked list, tree, executable code, script, or other data structure to store information. In some implementations, the data store 320 or a portion of the data store 320 may be distributed across one or more other devices including the computing devices 300, network attached storage devices, and so forth.

A communication module 322 may be configured to establish communications with one or more of other computing devices 300, the sensors 142, or other devices 150. The communications may be authenticated, encrypted, and so forth. The communication module 322 may also control the communication interfaces 308.

One or more of the data acquisition parameters 124, operating parameters 126, operating values 128, reference data 138, or the molecular concentration data 140 may be stored in the memory 316.

The memory 316 may also store the control module 122. As described above, the control module 122 may operate the RF circuitry 112 to produce operating values 128.

The memory 316 may store the data processing module 136. The data processing module 136 uses the operating values 128, the reference data 138, and so forth as input to generate the molecular concentration data 140.

In one implementation, the data processing module 136 may use reference data 138 to generate molecular concentration data 140 that is indicative of a concentration of one or more types of molecules 106 in the user 102.

In some implementations, a calibration process may be performed in which an external sensor is used to obtain external sensor data 326 that is indicative of a concentration of a type of molecule 106. For example, a blood glucose meter that uses a sample of a drop of blood may be used as the external sensor. At a contemporaneous time, the RF circuitry 112 may be used to obtain the operating values 128. The external sensor data 326 comprising concentration data from the external sensor may be used in conjunction with the operating values 128 to determine a correspondence between one or more operating values 128 and molecular concentration. This correspondence may be stored as the reference data 138. The reference data 138 may be specific to a particular user 102. For example, the reference data 138 may be specific to user "Pat". In some implementations, the reference data 138 may be processed using one or more techniques to interpolate values between those which have been measured. In some implementations, previously acquired reference data 138 may be used, and a calibration factor may be determined based on the reference data 138.

Threshold data 328 may be stored in the memory 316. The threshold data 328 may be used to designate a threshold to which molecular concentration data 140 may be compared. For example, the threshold data 328 may specify threshold values for particular types of molecules 106. If the molecular concentration data 140 is less than a first threshold or greater than a second threshold, the user interface module 144 may generate an alarm and present that information using the output device 148.

The user interface module 144 provides a user interface using one or more of the I/O devices 314. The user interface module 144 may be used to obtain input from the user 102, present information to the user 102, and so forth. For example, the user interface module 144 may present a graphical user interface on the display device 148(3) and accept user input using the touch sensor 142(4).

Continuing the earlier example, if the molecular concentration data 140 indicates that user's 102 blood glucose level is less than a threshold value, the user interface module 144 may present information indicative of this on the display device 148(3). The user 102 may then take corrective actions, such as consuming glucose to raise their blood sugar level, reducing activity, and so forth.

The computing device 300 may maintain historical data 330. For example, the historical data 330 may comprise the operating values 128, molecular concentration data 140, or data from one or more of the sensors 142 obtained at different times. The historical data 330 may be used to provide information about trends or changes over time. For example, the historical data 330 may comprise an indication of average daily blood glucose levels of the user 102 over a span of several weeks. The user 102 may then use this data to assist in managing their diet and insulin dosage.

Other modules 332 may also be present in the memory 316, as well as other data 334 in the data store 320.

In different implementations, different computing devices 300 may have different capabilities or capacities. For example, the other device 150 may have significantly more processor 304 capability and memory 316 capacity compared to the wearable device 104. In one implementation, the wearable device 104 may determine the operating values 128 and send those values to the other device 150. Other combinations of distribution of data processing and functionality may be used in other implementations.

Figure 4:
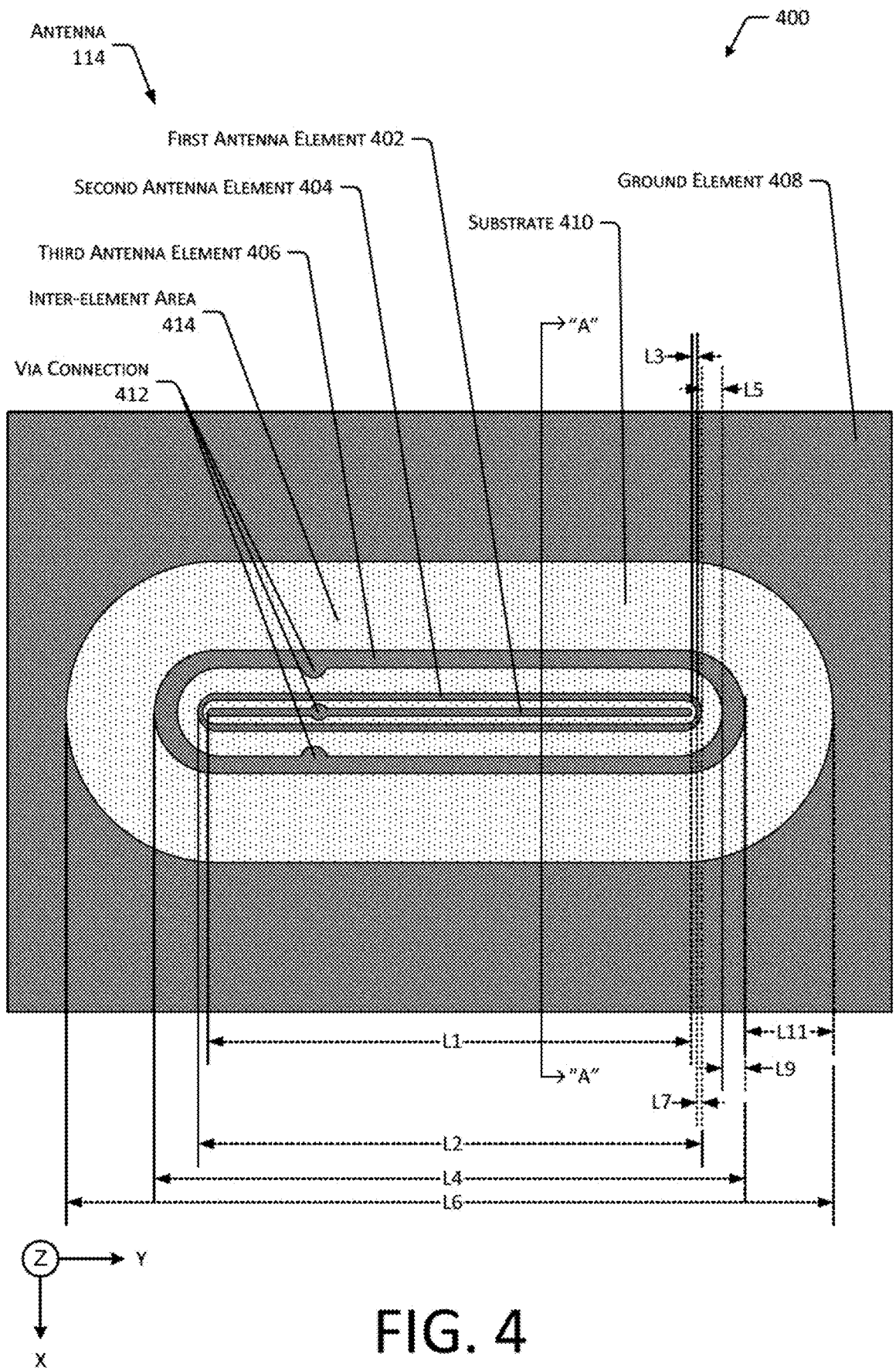
FIG. 4 illustrates one implementation of antenna elements in the antenna.

FIG. 4 illustrates a plan view 400 of one implementation of antenna elements in the antenna 114.

A first implementation of an antenna 114 is shown that comprises a first antenna element 402, a second antenna element 404, a third antenna element 406, and a ground element 408. The antenna 114 may comprise a substrate 410 that is electrically non-conductive. For example, the substrate 410 may comprise an insulator such as plastic or glass. The antenna elements may be on, affixed to, incorporated within, or otherwise maintained by the substrate 410. The substrate 410 may be rigid or flexible. For example, the substrate 410 may comprise a plastic layer upon which the antenna elements have been deposited. In one implementation the antenna 114 may comprise a flexible printed circuit with the antenna elements comprising traces thereon.

The first antenna element 402 may comprise a generally linear structure, having a first width and a first length L1. In the implementation shown here, the first length is greater than the first width. In other implementations, other configurations may be used.

The second antenna element 404 is arranged around the first antenna element 402. The second antenna element 404 has a second width and a second length L2. The second width is greater than the first width and L2 is greater than L1. The third antenna element 406 is arranged around the second antenna element 404. The third antenna element 406 has a third width and a third length L4. The third width is greater than the second width and L4 is greater than L2. A sixth length L6 is shown extending along a long axis of the antenna 114 from a first innermost edge of the ground element 408 at a first end of the long axis to a second innermost edge of the ground element 408 at a second end of the long axis.

A third length L3 is shown that is indicative of a distance or gap between an outermost edge of the first antenna element 402 and interior edge of the second antenna element 404. A fifth length L5 is shown that is indicative of a distance or gap between an outermost edge of the second antenna element 404 and an interior edge of the third antenna element 406. A seventh length L7 is indicative of a width of the second antenna element 404. A ninth length L9 is indicative of a width of the third antenna element 406. In some implementations L9 may be greater than L7. An eleventh length L11 is indicative of a distance or gap between an outermost edge of the third antenna element 406 and an interior edge of the ground element 408.

The ground element 408 is arranged around the third antenna element 406. In this implementation, the first antenna element 402 is linear. The second antenna element 404 forms an elongated oval or "racetrack" pattern with the first antenna element 402 nested within. The third antenna element 406 also forms an elongated oval of larger dimensions with the second antenna element 404 nested within. The edge of the ground element 408 around the third antenna element 406 also describes an elongated oval. For example, a distance between an outermost edge of the third antenna element 406 and an innermost edge of the ground element 408 may be constant. Continuing the example, for a given point on the outermost edge of the third antenna element 406, a tangent may be determined. A distance from the point and perpendicular to the tangent to the innermost edge of the ground element 408 may be constant for all points along the outermost edge of the third antenna element 406.

In the implementation depicted here, the overall arrangement of the antenna elements relative to the ground element 408 and one another is symmetrical with respect to at least two axes. In other implementations, other arrangements may be used. These arrangements may be asymmetrical in overall pattern, size of antenna elements, spacing between antenna elements, and so forth.

Also shown are via connections 412 that comprise enlarged portions of antenna elements to provide for electrical connectivity through vias to feedlines on a backside of the substrate 410 (not shown). For example, portions of the third antenna element 406 and the first antenna element 402 have larger surface areas to provide additional cross sectional areas for connection to the vias.

An inter-element area 414 is shown between two adjacent antenna elements. For example, there is a first inter-element area 414 between the first antenna element 402 and the second antenna element 404, a second inter-element area 414 between the second antenna element 404 and the third antenna element 406, and a third inter-element area 414 between the third antenna element 406 and the ground element 408.

The antenna 114 may comprise two or more antenna elements. While four antenna elements are depicted here, in other implementations the antenna 114 may include more or fewer antenna elements. In some implementations arrays of antennas 114 may be used. The arrays may include antennas 114 with different dimensions.

The dimensions of the antenna elements may be determined based on the sample depth desired during operation. For example, as the area of the antenna 114 increases, the electromagnetic field provided by the antenna 114 during operation may also increase, allowing measurement at increased depth.

One or more of the antenna elements may comprise closed loops as shown here. For example, the first antenna element 402 may comprise a rectangular area or strip while the second antenna element 404 comprises an electrically conductive ring. In other implementations, the second antenna element 404 may have at least one gap or electrically non-conductive region to form a split ring.

Figure 5:
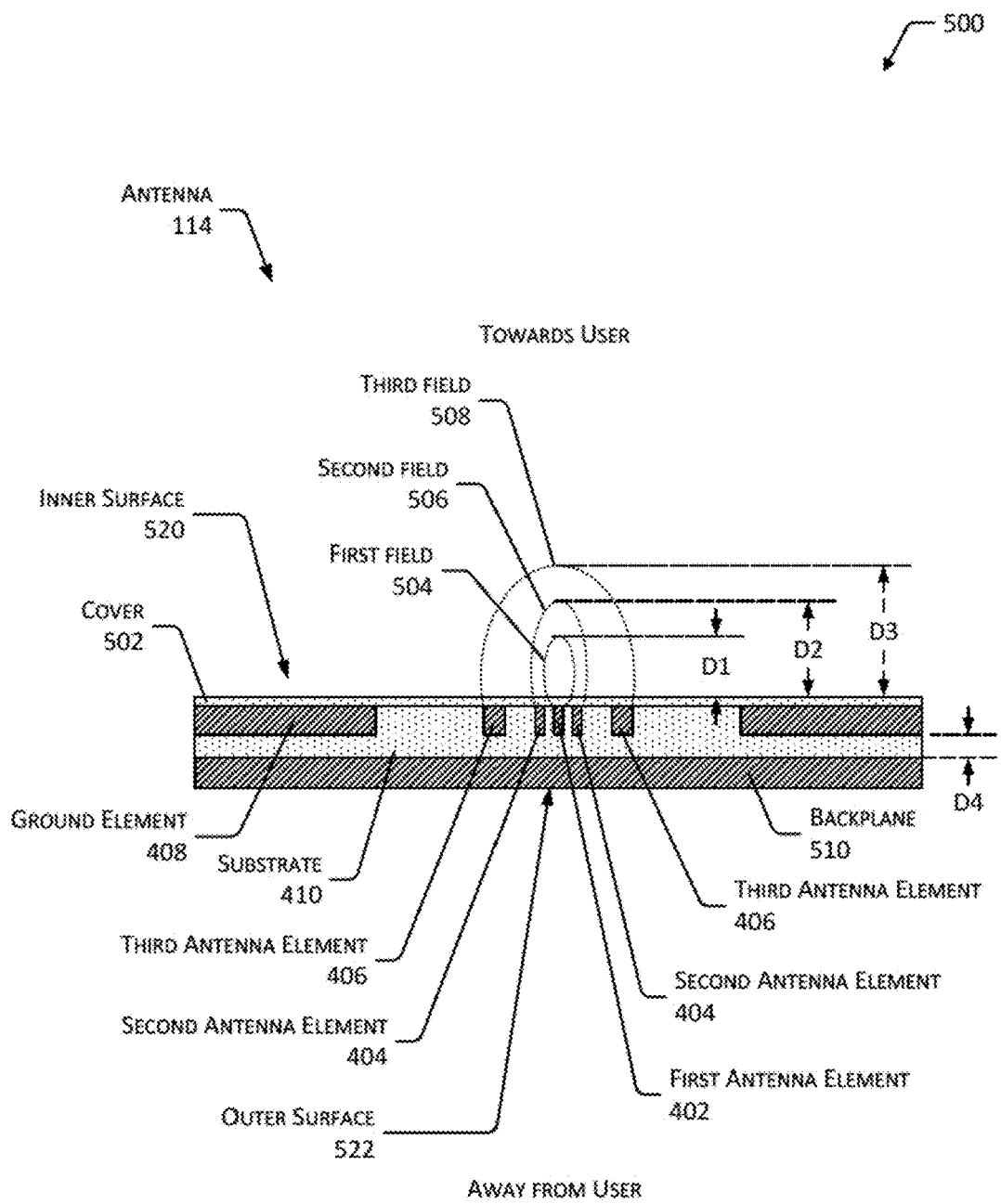
FIG. 5 illustrates a cross section of the antenna as shown in FIG. 4, according to one implementation.
Figure 5:
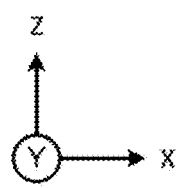

FIG. 5 illustrates a cross section 500 of the antenna 114 as shown in FIG. 4, along line A-A, according to one implementation. As described with regard to FIG. 4, the antenna 114 comprises the first antenna element 402, the second antenna element 404, the third antenna element 406, and the ground element 408 that are supported by the substrate 410. In some implementations the system may include a ground plane or shield that is located behind the substrate 410 (not shown here), on a side opposite where the user 102 will be during use. For example, the ground plane may comprise a sheet of electrically conductive material.

Also depicted, by way of illustration and not as a limitation, are corresponding electrical fields that would extend from the combination of various sets of antenna elements, as switched by the switching circuitry 118 during operation. A first field 504 corresponding to use of the first antenna element 402 is shown that extends a first distance D1 from the antenna 114. A second field 506 corresponding to use of the first antenna element 402 and the second antenna element 404 is shown that extends a second distance D2 from the antenna 114. The second distance D2 is greater than the first distance D1. A third field 508 corresponding to use of the first antenna element 402, the second antenna element 404, and the third antenna element 406 is shown that extends a third distance D3 from the antenna 114. The third distance D3 is greater than the second distance D2. By selecting different sets of antenna elements to use, different distances may be selected, allowing for measurement at different depths within the user 102.

The antenna elements may be located in a common plane, which may be designated as an antenna element layer. In other implementations one or more of the antenna elements may be positioned at different heights or have different thicknesses with respect to the substrate 410. The antenna 114 may comprise a backplane 510. The backplane 510 may comprise electrically conductive material on a side of the substrate 410 opposite the first antenna element 402, the second antenna element 404, and the third antenna element 406. A distance D4 between the antenna elements and the backplane 510 may affect the distances D1, D2, and D3. For example, as the distance D4 increases, the distances D1, D2, D3 may also increase.

In the implementation depicted here, an uppermost surface of the antenna elements is flush or even with the substrate 410. This provides a flat or planar surface that is level in cross section across the first antenna element 402, the second antenna element 404, the third antenna element 406, and the ground element 408. In one implementation, this arrangement may be provided by the substrate 410 extending upward, as shown here. In another implementation a filler material may be used. In yet another implementation, the substrate 410 may be etched, milled, or formed to provide recesses within which the antenna elements may be placed to provide the desired cross section. By providing this flat cross section, longevity of the device may be improved, user comfort may be improved, and so forth. For example, the flat cross section precludes protrusions or edges that could wear during relative motion between the user 102 and the antenna 114.

In some implementations a cover 502 may be used that is adjacent to the antenna elements and is between the antenna elements and the user 102. The cover 502 may comprise a non-conductive material. For example, the cover 502 may comprise plastic, glass, or another material that is transparent to the signal(s) 108. In some implementations the cover 502 may be omitted. In these implementations, the antenna elements may come into direct contact with the skin of the user 102. The antenna elements may comprise a biocompatible material such as gold, silver, rhodium, and so forth. In addition to being used to emit and acquire the signal 108, in implementations where the antenna elements are in contact with the user 102, they may be used to acquire other information. For example, galvanic skin conductivity may be measured using two or more antenna elements, cardiac electrical signals may be acquired using one or more of the antenna elements, and so forth.

During wear, the support structure 110 maintains an inner surface 520 of the antenna 114 proximate to a portion of the user 102 while the wearable device 104 is being worn. An outer surface 522 of the antenna 114 is opposite, away from the user 102.

Figure 6:
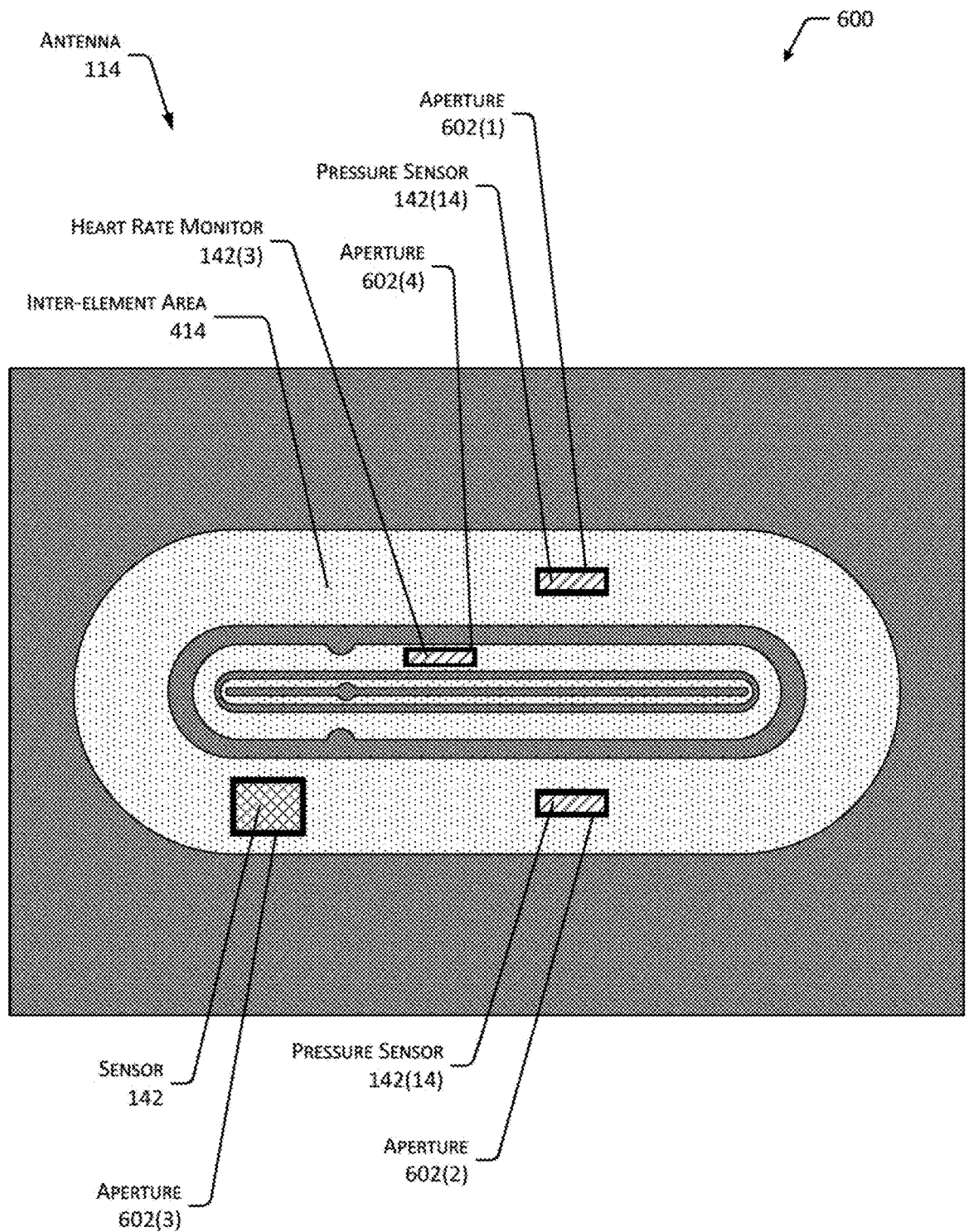
FIG. 6 illustrates some implementations of antenna elements in the antenna with apertures for other sensors, according to one implementation.

FIG. 6 illustrates at 600 some implementations of antenna elements in the antenna 114 with apertures for other sensors 142, according to one implementation. One or more apertures 602 or sensors 142 may be located within the inter-element area 414 of the antenna 114. The aperture 602 may provide a window or opening in the substrate 410 to facilitate operation of the wearable device 104. For example, the aperture 602 may provide a window through which an optical sensor such as a light emitting diode (LED) or a camera 142(7) is able to operate and acquire data about the user 102. In another example, the aperture 602 may be used by another sensor 142, such as a capacitive sensor, pressure sensor 142(14), and so forth. Some devices may be mounted to the substrate 410 or may be located between the antenna 114 and the user 102 during operation. For example, an LED may be affixed to the substrate 410 and when operated may illuminate a portion of the user 102 that is proximate to the inner surface of the wearable device 104.

In some implementations, sensors may operate through the substrate 410. For example, if the substrate 410 is flexible a pressure sensor 142(14) may operate through the substrate 410. In another example the substrate 410 may be transmissive to a signal being detected, such as a particular frequency of light.

Figure 7:
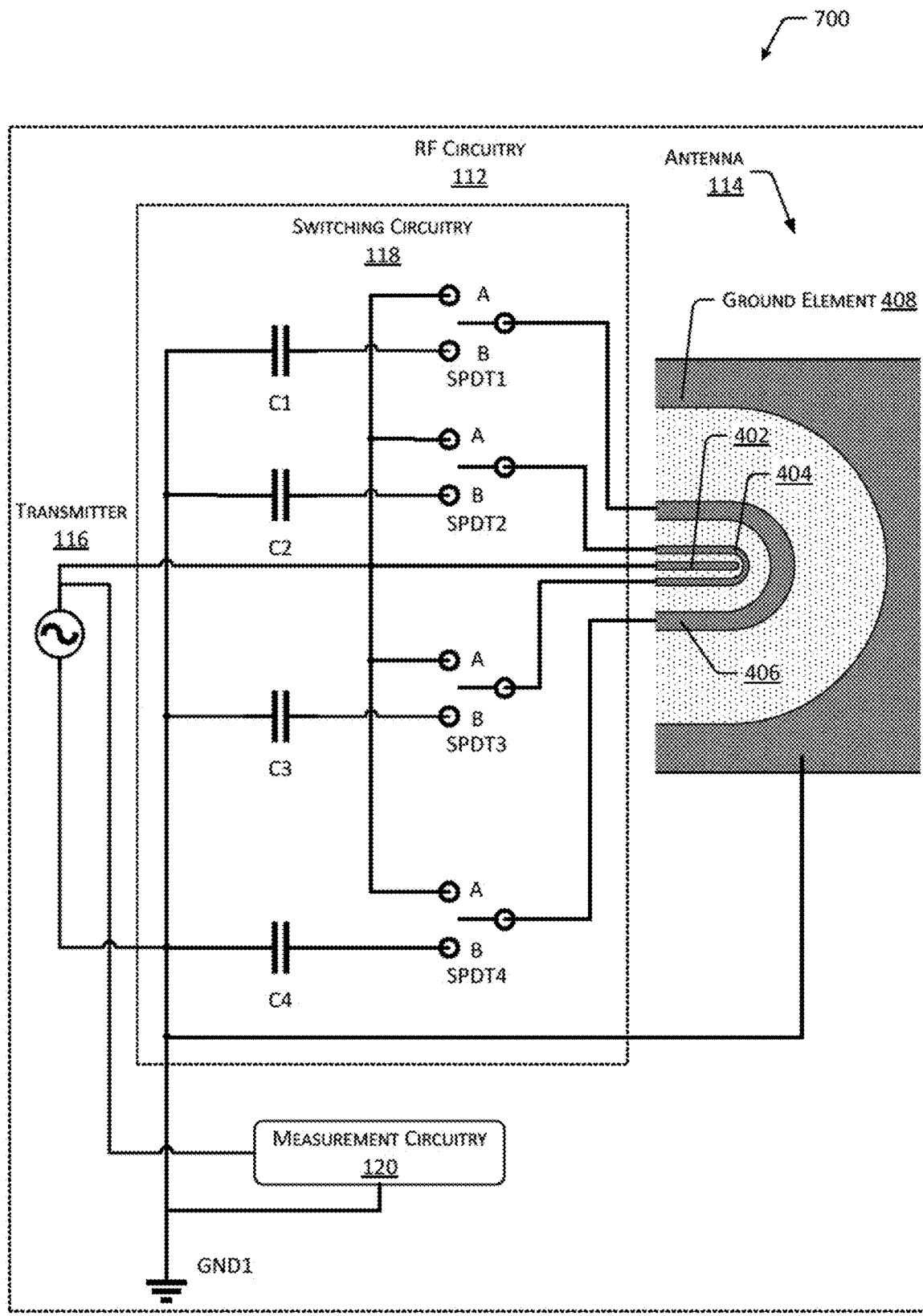
FIG. 7 is a circuit diagram of switching circuitry to select particular sets of antenna elements during operation, according to one implementation.

FIG. 7 is a circuit diagram 700 of the switching circuitry 118 to select particular sets of antenna elements of the antenna 114 during operation, according to one implementation. The switching circuitry 118 allows various combinations of the first antenna element 402 to be connected to one or more of the second antenna element 404 or the third antenna element 406. In this illustration, the switching circuitry 118 comprises four pairs of capacitors C1, C2, C3, and C4 and four single position double throw (SPDT) switches SPDT1, SPDT 2, SPDT3, and SPDT 4, or equivalent circuitry. Each SPDT has a first input terminal ("A") and a second input terminal ("B") and a single output terminal. In the implementation shown here, the first input terminal of each SPDT is connected to the output of the transmitter 116. The second input terminal of each SPDT is connected to a first terminal of a capacitor. A second terminal of each of the capacitors is connected to ground.

In some implementations, the switching circuitry 118 may be operated according to the following truth table:

TABLE 1

|  | SPDT1 | SPDT2 | SPDT3 | SPDT4 |
| --- | --- | --- | --- | --- |
| Long Mode | A | A | A | A |
| Medium Mode | B | A | A | B |
| Short Mode | B | B | B | B |

The transmitter 116 has a first terminal and a second terminal. The first terminal provides signal output and is connected to the first antenna element 402. The second terminal is connected to a ground.

The switching circuitry 118 comprises a third terminal connected to the first terminal and the first antenna element 402. A fourth terminal is connected to the second terminal, and is thus connected to ground.

A fifth terminal is connected to a first portion of the second antenna element 404. A sixth terminal is connected to a second portion of the second antenna element 404. A seventh terminal is connected to a first portion of the third antenna element 406. An eighth terminal is connected to a second portion of the third antenna element 406.

During operation, the switching circuitry 118 may be directed to selectively connect one or more of the antenna elements to the output of the transmitter 116. For example, at a first time, the switching circuitry 118 may operate to connect the third terminal to the fifth terminal, the sixth terminal, the seventh terminal, and the eighth terminal. Continuing the example, at a second time, the switching circuitry 118 may operate to connect the third terminal to the fifth terminal, and the sixth terminal. At the second time the fourth terminal is also connected to the seventh terminal and the eighth terminal. Continuing the example, at a third time, the switching circuitry may operate to connect the fourth terminal to the fifth terminal, the sixth terminal, the seventh terminal, and the eighth terminal.

Also shown is measurement circuitry 120. The measurement circuitry 120 is configured to determine the operating values 128 associated with operation of the transmitter 116 while connected to one or more of the antenna elements. For example, the measurement circuitry 120 may be configured to determine the impedance presented by the antenna 114 at a particular frequency.

Figure 8:
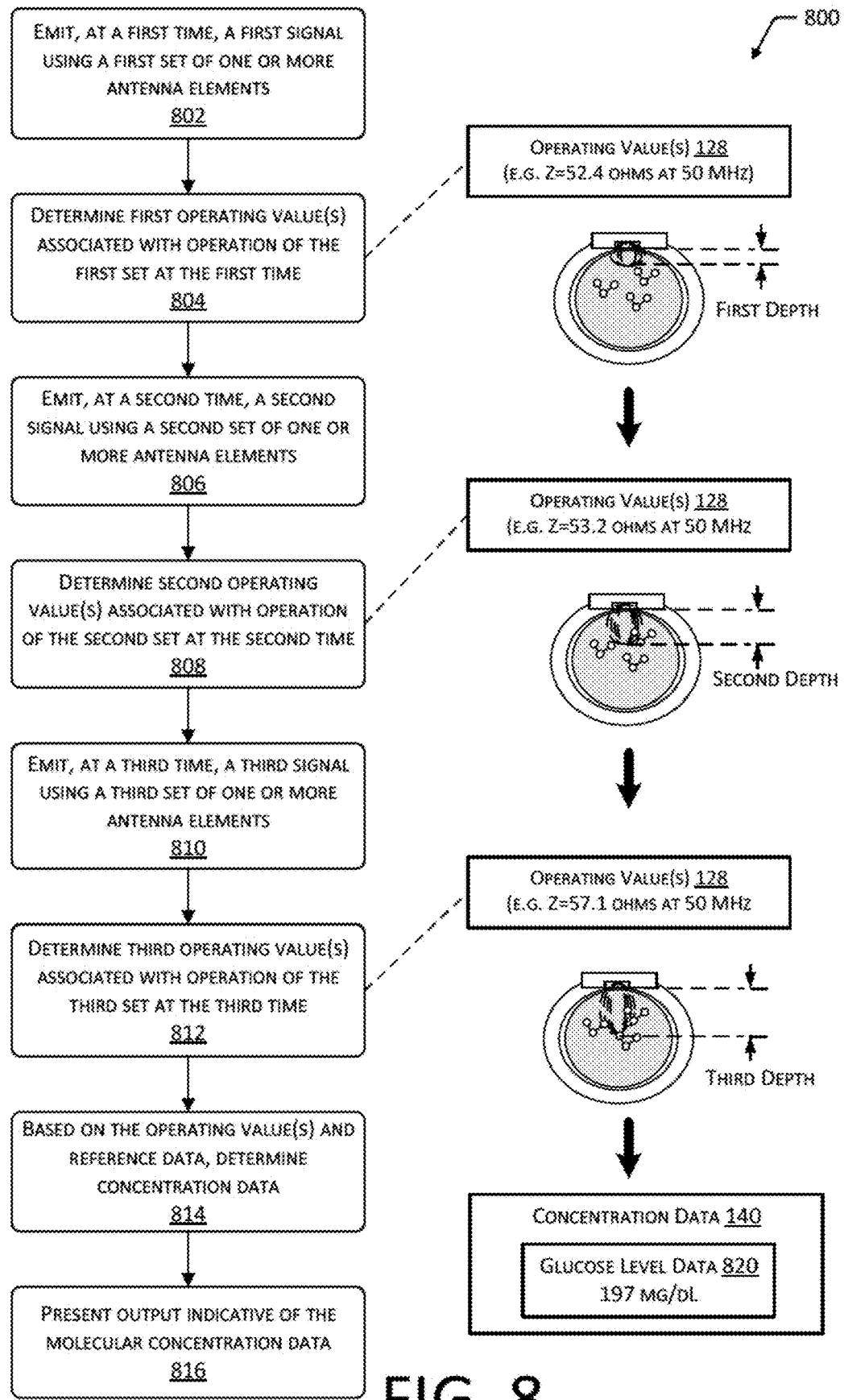
FIG. 8 illustrates a flow diagram of a process of using radio frequency signals emitted by the antenna to determine molecular concentration data, according to one implementation.

FIG. 8 illustrates a flow diagram 800 of a process of using radio frequency signals 108 emitted by the antenna 114 to determine molecular concentration data 140, according to one implementation. The process may be implemented at least in part by the wearable device 104.

At 802, a first signal 108 is emitted at a first time using a first set of one or more antenna elements. For example, the switching circuitry 118 may implement the "short mode" in which the first antenna element 402 is connected to the output of the transmitter 116 while the remaining antenna elements are connected to ground.

At 804, a first operating value 128 is determined that is associated with operation of the first set at the first time. For example, a first impedance presented by the first antenna element 402 to the transmitter 116 may be determined by the measurement circuitry 120.

At 806, a second signal 108 is emitted at a second time using a second set of one or more antenna elements. For example, the switching circuitry 118 may implement the "medium mode" in which the first antenna element 402 and the second antenna element 404 are both connected to the output of the transmitter 116 while the remaining third antenna element 406 is connected to ground.

At 808, a second operating value 128 is determined that is associated with operation of the second set at the second time. For example, the second impedance presented by the combination of the first antenna element 402 and the second antenna element 404 to the transmitter 116 may be determined by the measurement circuitry 120.

At 810, a third signal 108 is emitted at a third time using a third set of one or more antenna elements. For example, the switching circuitry 118 may implement the "long mode" in which the first antenna element 402, the second antenna element 404, and the third antenna element 406 are all connected to the output of the transmitter 116.

At 812, a third operating value 128 is determined that is associated with operation of the third set at the third time. For example, the third impedance presented by the combination of the first antenna element 402, the second antenna element 404, and the third antenna element 406 to the transmitter 116 may be determined by the measurement circuitry 120.

At 814, concentration data 140 is determined based on the operating values 128. For example, the operating values 128 may be used as inputs to the reference data 138 which provides as output the molecular concentration data 140. Continuing the example, the concentration data 140 may include glucose level data 820. In another example the operating value(s) 128 may be provided as input to a trained machine learning system which then provides as output the concentration data 140.

At 816 output indicative of the molecular concentration data 140 is presented. In one implementation, the user interface module 144 may generate output data 146 that is used by the one or more output devices 148 to present output to the user 102. For example, a graphical indication may be provided using a display device 148(3) of the other device 150.

Figure 9:
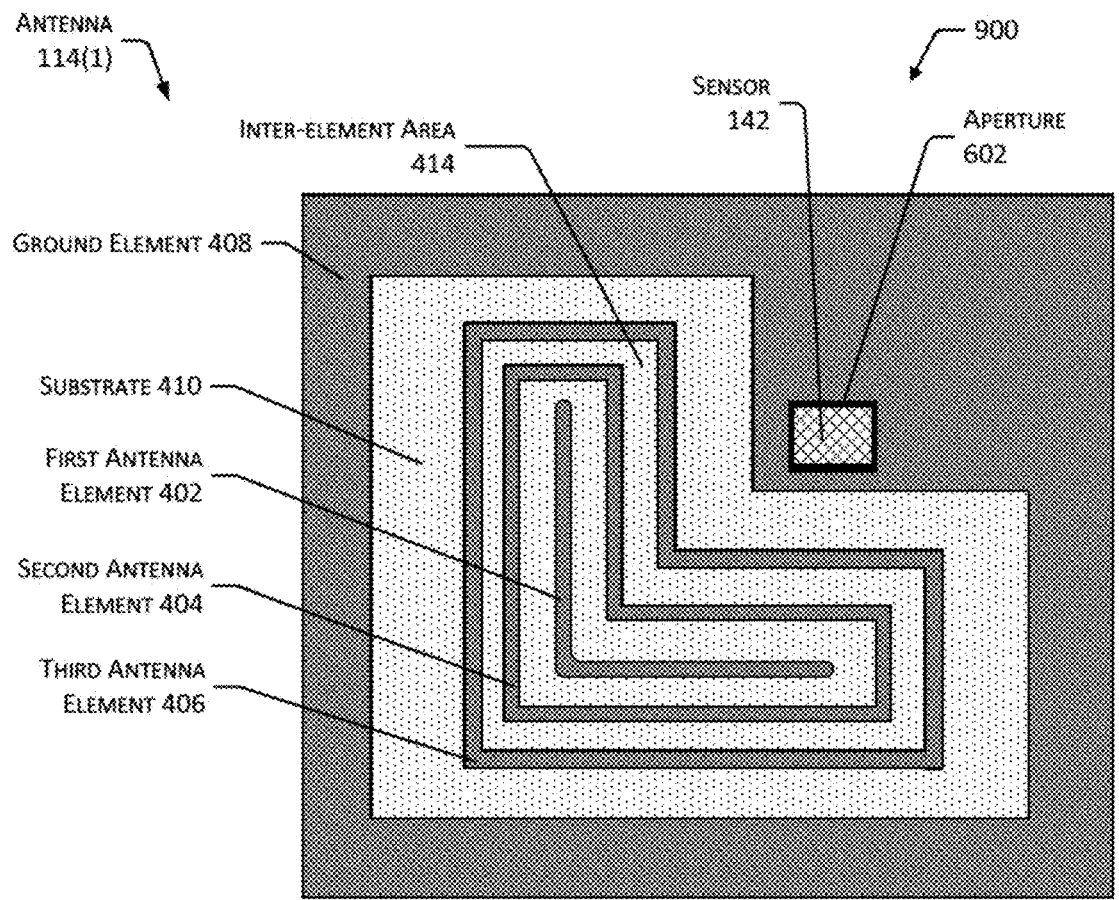
FIG. 9 illustrates other implementations of antenna elements in the antenna.
Figure 9:
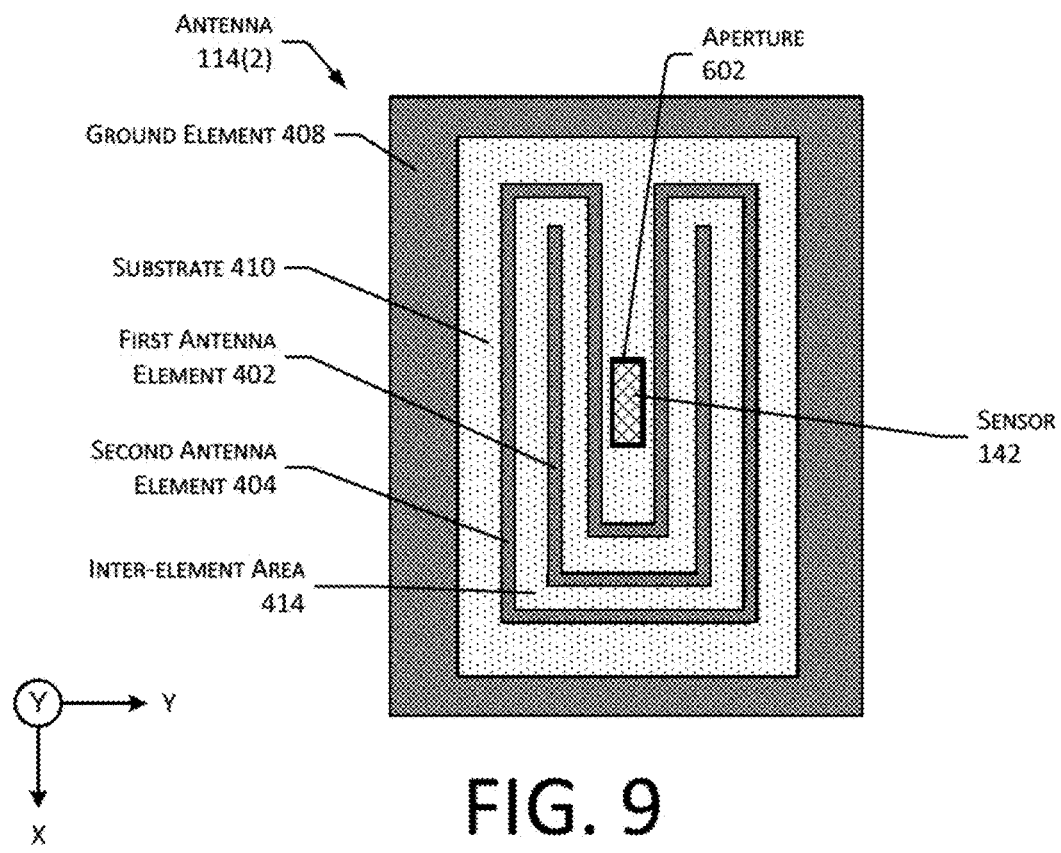

FIG. 9 illustrates plan views 900 of two implementations of antenna elements in the antenna 114.

In a first implementation, the antenna 114(1) comprises a first antenna element 402, a second antenna element 404, a third antenna element 406, and a ground element 408. The antenna 114(1) may comprise a substrate 410 that is electrically non-conductive. The antenna elements may be on, affixed to, incorporated within, or otherwise maintained by the substrate 410. The substrate 410 may be rigid or flexible. For example, the substrate 410 may comprise a plastic layer upon which the antenna elements have been deposited. In one implementation the antenna 114 may comprise a flexible printed circuit with the antenna elements comprising traces thereon.

The first antenna element 402 may comprise a generally "L" shaped structure, having a first portion and a second portion, with the first portion and the second portion forming an angle. The first portion and the second portion may be the same or different sizes. The second antenna element 404 forms a loop around the first antenna element 402 and is generally "L" shaped overall. The third antenna element 406 forms a loop around the second antenna element 404 and is generally "L" shaped overall. The ground element 408 is arranged around a perimeter of the third antenna element 406. An aperture 602 is shown in the ground element 408, with a sensor 142 disposed within or proximate to the aperture 602.

In a second implementation shown in FIG. 9, the antenna 114(2) comprises a first antenna element 402, a second antenna element 404, and a ground element 408. The antenna 114 may comprise N elements, where N is a nonzero positive integer value. For example, the antenna 114 may comprise 1, 2, 3, or 50 elements.

In the second implementation of the antenna 114(2), the first antenna element 402 may comprise a generally "U" shaped structure, having a first portion, a second portion, and a third portion. The first portion, the second portion, and the third portion may be the same or different sizes. The second antenna element 404 forms a loop around the first antenna element 402 and is generally "U" shaped overall. The ground element 408 is arranged approximately around a perimeter of the second antenna element 404. An aperture 602 is shown between portions of the second antenna element 404, with a sensor 142 disposed within or proximate to the aperture 602.

In other implementations, the antenna 114 may use elements arranged in other patterns. For example, the antenna 114 may comprise one or more serpentine elements, elements in a "W" shape, elements in an "H" shape, and so forth.

While the system and techniques described herein are used with respect to measure humans, it is understood that these techniques may be used to monitor other types of animals. In some implementations, the systems and techniques may be used to characterize other objects. For example, the system may be used to determine a sugar concentration in a fruit, water concentration in a mixture, and so forth.

The processes discussed herein may be implemented in hardware, software, or a combination thereof. In the context of software, the described operations represent computer-executable instructions stored on one or more non-transitory computer-readable storage media that, when executed by one or more processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described herein. The computer-readable storage medium may be one or more of an electronic storage medium, a magnetic storage medium, an optical storage medium, a quantum storage medium, and so forth. For example, the computer-readable storage media may include, but is not limited to, hard drives, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Thus, although certain steps have been described as being performed by certain devices, software programs, processes, or entities, this need not be the case, and a variety of alternative implementations will be understood by those having ordinary skill in the art.

Additionally, those having ordinary skill in the art will readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as illustrative forms of implementing the claims.

What is claimed is:

1. A device comprising:
an antenna comprising:
a first antenna element on a substrate;
a second antenna element on the substrate, wherein the second antenna element is arranged around the first antenna element; and
a third antenna element on the substrate, wherein the third antenna element is arranged around the second antenna element;
a transmitter having a first output;
first circuitry to couple the first output of the transmitter to one or more of the first antenna element, the second antenna element, or the third antenna element;
second circuitry to measure one or more operating values associated with operation of the transmitter;
a first memory, storing computer-executable instructions; and
a first hardware processor, wherein the first hardware processor executes the computer-executable instructions to:
operate the first circuitry to couple the first output of the transmitter to the one or more of the first antenna element, the second antenna element, or the third antenna element; and
operate the second circuitry to determine the one or more operating values associated with operation of the transmitter.

2. The device of claim 1, wherein:
the first antenna element has a first width and a first length, further wherein the first length is greater than the first width; and
the second antenna element has a second width and a second length, further wherein:
the second width is greater than the first width and the second length is greater than the first length, and
the second antenna element is arranged in an elongated oval around the first antenna element, and
the third antenna element has a third width and a third length, further wherein:
the third width is greater than the second width,
the third length is greater than the second length, and
the third antenna element is arranged in an elongated oval around the second antenna element.

3. The device of claim 1, further comprising:
a ground element affixed to the substrate, wherein the ground element is arranged around the third antenna element.

4. The device of claim 1, further comprising:
a pressure sensor;
wherein the first hardware processor executes the computer-executable instructions to:
receive data from the pressure sensor; and
determine, based on the data, that at least a portion of the device is in contact with an object; and
wherein the transmitter is operated based at least in part on the data that indicates that the at least a portion of the device is in contact with the object.

5. The device of claim 1, wherein the one or more operating values are indicative of an impedance presented by the antenna.

6. The device of claim 1, wherein the first hardware processor executes the computer-executable instructions to:
operate the first circuitry to couple the first output of the transmitter to the first antenna element at a first time;
operate the transmitter to generate a first signal at the first time;
operate the first circuitry to couple the first output of the transmitter to the first antenna element and the second antenna element at a second time;
operate the transmitter to generate a second signal at the second time;
operate the first circuitry to couple the first output of the transmitter to the first antenna element, the second antenna element, and the third antenna element at a third time; and
operate the transmitter to generate a third signal at the third time.

7. The device of claim 1, wherein the first hardware processor executes the computer-executable instructions to:
determine a first sample depth;
determine, based on the first sample depth, an antenna configuration indicative of a first set of one or more antenna elements to connect to the transmitter; and
operate the first circuitry based on the antenna configuration.

8. The device of claim 1, wherein the second antenna element and the third antenna element each comprise a closed loop of electrically conductive material.

9. The device of claim 1, further comprising:
an aperture in the substrate between one or more of:
the first antenna element and the second antenna element, or
the second antenna element and the third antenna element; and
a sensor proximate to the aperture.

10. The device of claim 1, wherein the antenna comprises a long axis that extends lengthwise through a longest axis of the first antenna element,
the device further comprising:
a support structure that is configured to retain the device proximate to an arm of a user with the long axis of the antenna parallel to a long axis of the arm.

11. The device of claim 1, further comprising:
a cover, wherein the first antenna element, the second antenna element, and the third antenna element are between the cover and the substrate; and
wherein the cover is supported at least in part by one or more of:
a portion of the substrate that is level in cross section with the first antenna element, the second antenna element, and the third antenna element, or
a filler material that is level in cross section with the first antenna element, the second antenna element, and the third antenna element.

12. A device comprising:
a first antenna element;
a second antenna element arranged in an elongated oval around the first antenna element;
a transmitter having a first output;
first circuitry to couple the first output of the transmitter to one or more of the first antenna element or the second antenna element;
second circuitry to measure one or more values associated with operation of the transmitter;
at least one memory, storing computer-executable instructions; and
at least one hardware processor, wherein the at least one hardware processor executes the computer-executable instructions to:

operate the first circuitry;
operate the second circuitry;
operate the transmitter to generate one or more signals; and
determine the one or more values associated with operation of the transmitter.

13. The device of claim 12, wherein the first antenna element is positioned in a first plane and the second antenna element is positioned in the first plane.

14. The device of claim 12, wherein:
the first antenna element has a first width and a first length, further wherein the first length is greater than the first width;
the second antenna element has a second width and a second length, further wherein:
the second width is greater than the first width, and
the second length is greater than the first length, and
the device further comprising:
a ground element affixed to a substrate, wherein the ground element is arranged around the second antenna element.

15. The device of claim 12, wherein the one or more values are indicative of an impedance to the one or more signals that are provided to one or more of: the first antenna element or the second antenna element.

16. The device of claim 12, wherein the at least one hardware processor executes the computer-executable instructions to:
operate the first circuitry to couple the first output of the transmitter to the first antenna element at a first time;
operate the transmitter to generate a first signal at the first time;
operate the first circuitry to couple the first output of the transmitter to the first antenna element and the second antenna element at a second time; and
operate the transmitter to generate a second signal at the second time.

17. The device of claim 12, wherein a long axis of the second antenna element extends lengthwise through a longest axis of the first antenna element,
the device further comprising:
a support structure that is configured to retain the device proximate to an arm of a user with the long axis of the first antenna element parallel to a long axis of the arm.

18. A device comprising:
a first antenna element;
a second antenna element arranged around the first antenna element;
a transmitter;
circuitry associated with the first antenna element, the second antenna element, and the transmitter;
at least one memory storing computer-executable instructions; and
at least one hardware processor, wherein the at least one hardware processor executes the computer-executable instructions to:
operate the circuitry to couple the transmitter to the first antenna element at a first time;
operate the transmitter to generate a first signal at the first time;
operate the circuitry to couple the transmitter to the first antenna element and the second antenna element at a second time;
operate the transmitter to generate a second signal at the second time; and
determine one or more values associated with operation of the transmitter.

19. The device of claim 18, wherein:
the first antenna element has a first length and a first width;
the second antenna element has a second length and a second width;
the second length is greater than the first length;
the second width is greater than the first width; and
the second antenna element is arranged in an elongated oval around the first antenna element.

20. The device of claim 18, further comprising:
a ground element arranged around the second antenna element.

* * * * *